United States Patent [19]
Volk

[11] Patent Number: 4,913,545
[45] Date of Patent: Apr. 3, 1990

[54] ADAPTER FOR LENS RETAINING RING FOR USE IN CONNECTION WITH EYE EXAMINATION

[76] Inventor: Donald A. Volk, 6805 Mayfield Rd., Apt. 1019, Mayfield Heights, Ohio 44124

[21] Appl. No.: 254,286

[22] Filed: Oct. 6, 1988

[51] Int. Cl.$^4$ ............................................. A61B 3/10
[52] U.S. Cl. ..................................... 351/205; 351/219
[58] Field of Search ....................... 351/205, 219, 223; 128/20, 341, 898

[56] References Cited

U.S. PATENT DOCUMENTS 4,721,378  1/1988  Volk ..................................... 351/205
4,728,183  3/1988  Heacock et al. ..................... 351/219

OTHER PUBLICATIONS

Sheet from inventor entitled Additional Prior Art with attached copy of Brochure page of *Ocular Instruments Inc.*, entitled *Argon Laser Lenses.*

Primary Examiner—P. M. Dzierzynski
Attorney, Agent, or Firm—Baldwin, Egan & Fetzer

[57] ABSTRACT

An adapter for a lens retaining ring and associated indirect ophthalmoscopy lens used by an examiner or practitioner during examination of a patient's eye fundus with a biomicroscope. The adapter includes a body portion for spacing the lens mounted in the retaining ring a predetermined distance from the eye of the patient when the adapter-retaining ring-lens combination is positioned against the eye of the patient under examination. The adapter is adapted to engage the eyelids of the eye under examination, and is so constructed so as to aid in maintaining such eyelids open, and openings are provided in the body of the adapter to aid in preventing fogging of the lens mounted in the lens retaining ring. The adapter may be selectively removable from the associated lens retaining ring (which may be a conventional or known lens retaining ring) or may be integrally formed with the retaining ring.

14 Claims, 1 Drawing Sheet

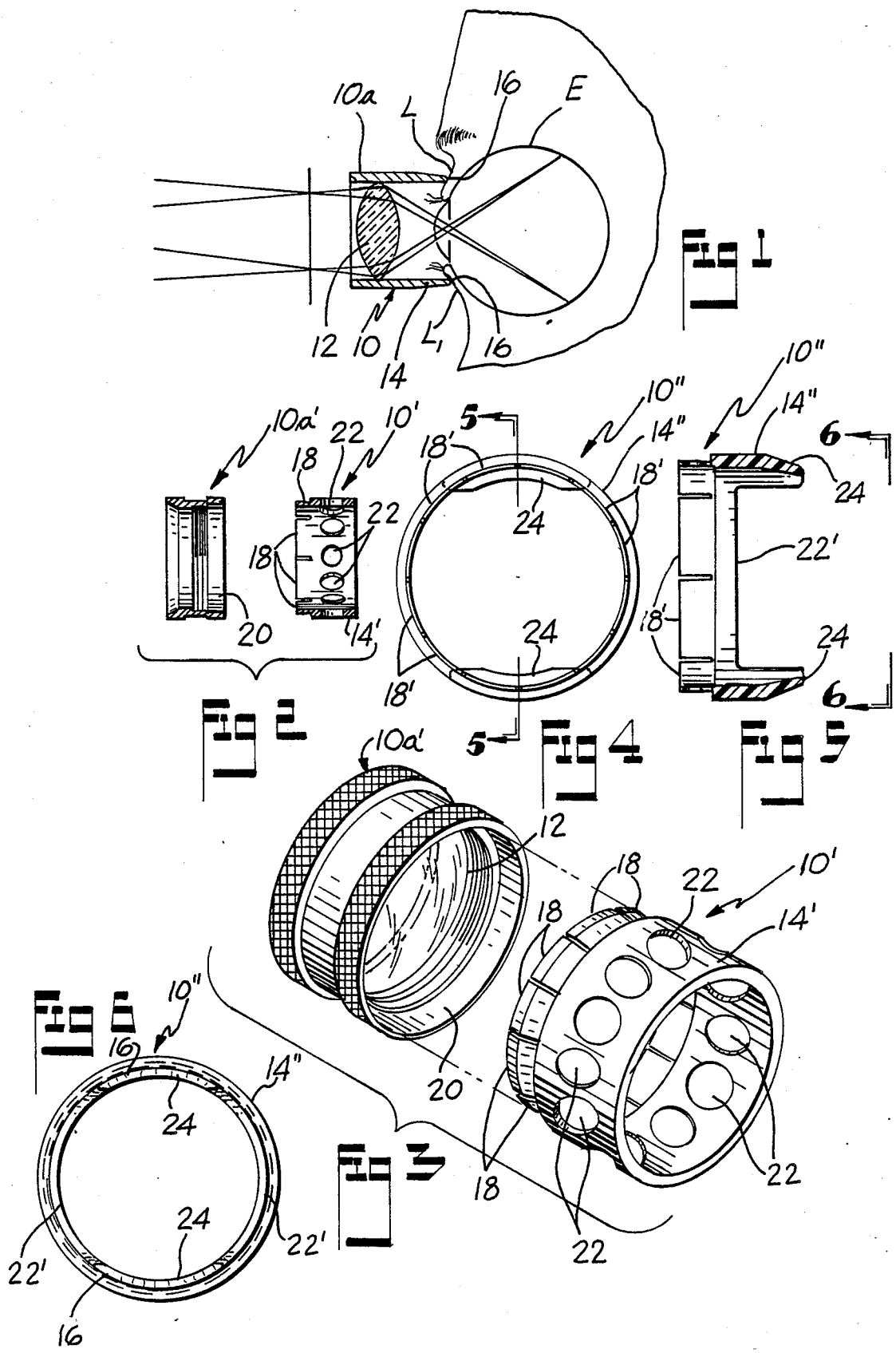

ADAPTER FOR LENS RETAINING RING FOR USE IN CONNECTION WITH EYE EXAMINATION

This invention relates in general to lens positioning devices for use in examination by an examiner or practitioner of a patient's eye fundus, such as for instance biomicroscopy of the eye, and more particularly relates to an adapter device for a lens retaining ring supporting an associated indirect opthalmoscopy lens, that is operable to maintain the lens and lens retaining ring a predetermined distance from the eye of the patient when the device is positioned against the eyelids of the eye under examination, and which is operable to aid in maintaining such eyelids open, thus facilitating the examination of the eye. The adapter device may be a separate unit adapted for ready coupling to and uncoupling from a conventional lens retaining ring, or the adapter device may be formed integrally with a lens retaining ring that is adapted to hold an associated lens.

BACKGROUND OF THE INVENTION

It is known in the prior art for the examiner or practioner to manually hold an indirect ophthalmoscopy lens with respect to the patient's eye during fundus examination, utilizing a biomicroscope, and such is conventional procedure utilized by many ophthalmologists and optometrists.

It is also known in the prior art to utilize a mechanical holder for positioning a lens relative to the patient's eye. In applicant's U.S. patent application Ser. No. 211,353 filed June 24, 1988 and entitled Lens Positioning Device For Indirect Biomicroscopy Of The Eye, such a holder mechanism is disclosed.

It is also known in the prior art to provide a device consisting of a corneal contacting portion and an aerial image forming portion, and wherein the device is hand held against the cornea and requires anesthetization of the eye.

SUMMARY OF THE INVENTION

The present invention provides an adapter for use with the lens retaining ring and associated lens, so as to maintain the lens and lens retaining ring a predetermined distance from the eye of the patient during examination of the eye by the practitioner, and which includes means for engaging the eyelids of the eye under examination for aiding in maintaining the engaged eyelids open, thus facilitating the examination, and wherein means is provided on the adapter to aid in preventing fogging of the lens during such eye examination.

Accordingly, an object of the invention is to provide a novel lens positioning adapter device for use in examination of the eye.

Another object of he invention is to provide a lens positioning device of the latter type which is readily attachable to and removable from a lens retaining ring and associated lens.

A still further object of the invention is to provide a device of the above described type which includes means for engaging with the eyelids of the eye under examination for aiding in holding such eyelids open during the practitioner's examination of the eye.

Another object of the invention is to provide an adapter of the aforementioned type which includes means for aiding in preventing fogging of the lens in the lens retaining ring during the eye examination.

A still further object of the invention is to provide an adapter of the aforedescribed type which is readily handled by the practitioner, which is comfortable to the patient, and which also can be utilized with mechanical holder of the general type described in applicant's aforementioned patent application Ser. No. 211,353.

Another object of the invention is to provide an adapter of the aforementioned type which is formed of generally flexible material, such as either transparent or opaque plastic defining rearwardly extending leg or finger portions which are generally squeezable together and positionable against the eyelids of a patient's eye, and when released, or pressed against the eyelids, move outwardly relative to one another to aid in holding the eyelids open.

Other objects and advantages of the invention will be apparent from the following description taken in conjunction with the accompanying drawings wherein:

BRIEF DESCRIPTION OF THE DRAWINGS

FIG. 1 is a diagrammatic, sectional illustration of a combined lens retaining ring and lens, and adapter positioned against the eyelids of a patient's eye during examination thereof by a practitioner, and embodying the invention;

FIG. 2 is a sectional, elevational, exploded view of an adapter device embodying the invention and having been detached from a conventional lens retaining ring;

FIG. 3 is an enlarged, perspective view of the detachable adapter and lens retaining ring and lens, of the FIG. 2 embodiment;

FIG. 4 is an enlarged, end elevational view, taken from the left hand end of FIG. 5, and illustrating another embodiment of detachable adapter device, adapted for coupling to a lens retaining ring of the type illustrated in FIGS. 2 and 3;

FIG. 5 is a vertical sectional view taken generally along line 5—5 of FIG. 4, looking in the direction of the arrows; and FIG. 6 is an end elevational view of the adapter device of FIG. 5, taken generally along line 6—6 of FIG. 5, looking in the direction of the arrows.

DESCRIPTION OF PREFERRED EMBODIMENT AND ALTERNATE EMBODIMENTS

Referring now again to the drawings, there is illustrated in FIG. 1 the eye E of the patient under examination by the practitioner, with the upper and lower eyelids L and L" of the eye engaged by the adapter 10 embodying the invention, and aiding in holding the eyelids in open condition to facilitate examination of the eye by the practitioner.

In this embodiment, the adapter 10 is formed integrally, or as a unit, with a lens retaining ring section 10a mounting a lens 12 therein in the conventional manner.

The adapter comprises a body portion 14 of tubular configuration projecting rearwardly from the lens retaining ring section 10a and providing for positioning the lens retaining ring section 10a and associated lens 12, a predetermined distance from the eye under examination.

The rear end of body portion 14 is of full circle configuration, in this embodiment, and engages the eyelids L, L" in generally spaced relation to the respective eyelashes of the lids, and as shown.

Such full circle end at its engagement with the eyelids, in this embodiment, is preferably of rounded configuration in side elevation (as at 16) and as shown, to increase the comfort to the lids at the engagement therewith. A preferred diameter dimension of said full circle, lid engaging end of the adapter is approximately 0.925 inches.

The adapter 10 and associated retaining ring and lens, may be manually held by the practitioner against the eyelids of the patient during examination, or the adapter and associated retaining ring and lens may be mechanically held by a mechanical holder, such as that of the general type of applicant's aforementioned pending patent application, while being manipulated by the practitioner.

FIG. 1 illustrates the fundus aerial image forming lens 12 positioned by the adapter, at, or approximately at, its back focal length from the pupil of the eye, or such that the generally maximum fundus field of view is available. This predetermined distance will vary according to the power or focal length of the particular lens held by the retaining ring section 10a.

FIGS. 2 and 3 disclose another embodiment wherein the adapter 10' is detachable from the lens retaining ring section 10a', and wherein yieldable tabs 18 extend forwardly from the body 14' of the adapter and are adapted to be received in snug frictional coupling relation with the interior peripheral surface 20 of known or conventional lens retaining ring 10a' to detachably hold the retaining ring and lens and adapter 10' together as a unit.

Openings 22 are preferably provided in body 14', to provide for circulation of air into the interior of body 14' when the device is being held against the lids of the eye undergoing examination, to aid in preventing fogging of the lens 12. In the embodiment illustrated, the rearward full circle end of the adapter 10' is not illustrated as being rounded in elevation, where engagement with the eyelids is adapted to occur, but such lid engaging end could be of rounded configuration similar to that as at 16 in the FIG. 1 integral embodiment of adapter. In other respects, the FIGS. 2 and 3 adapter may be generally similar to that of the FIG. 1 embodiment.

FIGS. 4–6 disclose a further detachable embodiment of adapter 10", which is formed of flexible material, such as flexible plastic, many types of which are known in the plastics art, and wherein the body portion 14" has recesses 22' formed therein providing the convection means for entry of circulating air into and from the interior of the adapter to prevent fogging of the lens held by an associated lens retaining ring (e.g. 10a').

Recesses or cut-outs 22' define rearwardly extending leg portions 24 on the adapter, spaced at approximately 180° from one another and adapted to engage the upper and lower eyelids L and L' respectively, when the adapter and coupled lens retaining ring and lens is held by the practitioner against the eyelids during examination of the patient's eye. In this connection, if the adapter 10" is formed of generally flexible plastic, the fingers of the practitioner can squeeze the leg portions 24 toward one another prior to placing the adapter, or more particularly the rearward ends of the leg portions against the eyelids of the patient, and then engage the eyelids with the upper and lower leg portions, after which release of the leg portions by the practitioner will permit the leg portions to spring apart to further aid to hold the eyelids of the eye being examined open.

Also the material of a flexible adapter of the type as that of adapter 10", may provide for outward deformation of the flexible leg portions thereof from one another produced by direct pressure applied by the adapter unit against the eyelids of the patient's eye under examination, thus causing opening of the eyelids and/or retention of the latter in open condition.

Adapted 10" can embody resilient or yieldable tabs 18' similarly to the FIG. 2 embodiment, and of sufficient rigidity, to provide for detachably coupling the adapter to a retaining ring and lens assembly (e.g. 10a').

From the foregoing description and accompanying drawings it will be seen that the invention provides a novel adapter device for a lens retaining ring for use in connection with an indirect eye fundus examination, comprising means adapted for coaction with the lens retaining ring for positioning the lens retaining ring and associated lens a predetermined distance from the eye of a patient under examination, together with means on the adapter for aiding in maintaining the eyelids of the patient's eye under examination, open.

The invention also provides an adapter device of the aforedescribed type which includes means aiding in preventing fogging of the associated lens during the eye examination, and in certain embodiments of the adapter, an adapter that can be conveniently and rapidly coupled to and/or uncoupled from an associated lens retaining portion of the device.

The adapter may be formed of any suitable material, such as metal or plastics, and if formed of metal is preferably formed of lightweight metal, such as for instance aluminum.

The terms and expressions which have been used are used as terms of description and not of limitation, and there is no intention in the use of such terms and expressions of excluding any equivalents of any of the features shown or described, or portions thereof, and it is recognized that various modifications are possible within the scope of the invention claimed.

I claim:

1. An adapter for a lens retaining ring comprising means for coaction with the lens retaining ring, providing positioning of the lens retaining ring and associated lens a predetermined distance from an eye of a patient under examination, and a means on said adapter for aiding in maintaining the eyelids of the patient's eye open by engaging the external eyelids of the eye under examination.

2. An adapter in accordance with claim 1 including means on said adapter for aiding in preventing fogging of the associated lens of the lens retaining ring.

3. An adapter in accordance with claim 2 wherein the last mentioned means comprises openings in said adapter providing for circulation of air into said adapter from exteriorly thereof, when said adapter is engaged with the patient's eyelids of the eye under examination.

4. An adapter in accordance with claim 1 wherein the last mentioned means comprises a generally circular portion, in end elevation, of the adapter, adapted for generally full circle engagement with the patient's external eyelids of the eye under examination.

5. An adapter in accordance with claim 1 wherein the last mentioned means comprises spaced upper and lower leg portions extending outwardly from said adapter in a direction away from said retaining ring, said leg portions being adapted for engagement with respectively the upper and lower eyelids of the patient's eye under examination in generally spaced relation to the eyelashes of such eye.

6. An adapter in accordance with claim 5 wherein said leg portions are flexible so that they can (a) be deformed inwardly toward one another by a practitioner before being engaged with the patient's eyelids and upon release of said leg portions the latter will spring outwardly relatively to one another or so that they can (b) be deformed outwardly away from one another by means of direct pressure of the unit against the eyelids.

7. An adapter in accordance with claim 1 which is integral with said lens retaining ring.

8. An adapter in accordance with claim 1 including means for detachable connecting said adapter to a lens retaining ring.

9. An adapter in accordance with claim 8 wherein the last mentioned means comprises yieldable tabs projecting outwardly from one end of the body of the adapter and adapted to be received in frictional holding coaction with the interior surface of the confronting end of the lens retaining ring.

10. An adapter in accordance with claim 9 formed of plastic.

11. An adapter in accordance with claim formed of metal.

12. An adapter in accordance with claim 1 wherein the last mentioned means comprises a full circle end of the body of said adapter, said full circle end being adapted for engagement with the external eyelids of the patient's eye under examination and having a diameter of approximately 0.925 inches, with the eye lid engaging end being rounded at the areas of engagement with the patient's eyelids.

13. An adapter in accordance with claim 1 wherein the last mentioned means comprises a semi-circle or portion of a circle engageable with the external eyelids, said adapter providing both ventilation as well as visibility of the patient's eye by the practitioner.

14. An adapter in accordance with claim 1 in combination with a lens retaining ring and lens, the first mentioned means providing for positioning said legs at or approximately at its back focal length from the pupil of the eye under examination.

* * * * *